United States Patent
Rutter

(10) Patent No.: US 7,591,830 B2
(45) Date of Patent: Sep. 22, 2009

(54) AIRWAY BALLOON DILATOR

(76) Inventor: Michael John Rutter, 1110 Brayton Ave., Cincinnati, OH (US) 45215

( * ) Notice: Subject to any disclaimer, the term of this patent is extended or adjusted under 35 U.S.C. 154(b) by 149 days.

(21) Appl. No.: 11/533,562

(22) Filed: Sep. 20, 2006

(65) Prior Publication Data

US 2007/0066962 A1  Mar. 22, 2007

Related U.S. Application Data

(63) Continuation-in-part of application No. 11/231,457, filed on Sep. 21, 2005, now abandoned.

(51) Int. Cl.
*A61M 29/00* (2006.01)
(52) U.S. Cl. .................. 606/191; 128/207.15
(58) Field of Classification Search ................ 606/159, 606/170, 174, 167, 191–198; 604/96.01–103.01; 128/207.14, 207.15
See application file for complete search history.

(56) References Cited

U.S. PATENT DOCUMENTS

| | | | |
|---|---|---|---|
| 3,173,418 A | 3/1965 | Baran | |
| 3,348,542 A | 10/1967 | Jackson | |
| 3,499,450 A | 3/1970 | Rathjen | |
| 3,640,282 A | 2/1972 | Kamen et al. | |
| 3,693,624 A * | 9/1972 | Shiley et al. | ........... 128/207.15 |
| 4,289,128 A | 9/1981 | Rusch | |
| 4,484,579 A | 11/1984 | Meno et al. | |
| 4,511,354 A | 4/1985 | Sterling | |
| 4,791,923 A | 12/1988 | Shapiro | |
| 4,953,548 A | 9/1990 | Stoddard et al. | |
| 4,983,167 A * | 1/1991 | Sahota | ....................... 606/194 |
| 5,040,531 A | 8/1991 | Coleman et al. | |
| 5,196,024 A | 3/1993 | Barath | |
| 5,222,966 A * | 6/1993 | Perkins et al. | ............... 606/159 |
| 5,251,619 A | 10/1993 | Lee | |
| 5,320,634 A | 6/1994 | Vigil et al. | |
| 5,392,774 A | 2/1995 | Sato | |
| 5,638,813 A | 6/1997 | Augustine | |
| 5,904,679 A | 5/1999 | Clayman | |
| 6,632,231 B2 | 10/2003 | Radisch, Jr. | |

* cited by examiner

*Primary Examiner*—Kevin T Truong
(74) *Attorney, Agent, or Firm*—Hasse & Nesbitt LLC; Donald E. Hasse; Ronald J. Richter

(57) ABSTRACT

A medical apparatus for widening a stenosis in the airway of a patient which includes a central hollow core, an inflatable outer balloon, and at least one inner balloon inside the outer balloon. The apparatus also can include a flexible support member mounted on the external surface of the outer balloon with at least one microsurgical blade. The outer balloon can be dumbbell-shaped to keep the balloon in position over the stenosis when the balloon is inflated. The hollow core allows the patient to be ventilated during the procedure, the inner balloon(s) allow higher dilation pressures to be generated from inside the outer balloon, and the blade can form an effective cutting edge upon inflation of the outer balloon.

20 Claims, 3 Drawing Sheets

AIRWAY BALLOON DILATOR

CROSS-REFERENCE TO RELATED APPLICATION

This application is a continuation-in-part of application Ser. No. 11/231,457, filed on Sep. 21, 2005 now abandoned.

FIELD OF THE INVENTION

The present invention relates to medical care for the larynx, trachea or bronchi to relieve a stenosis. In particular, the invention relates to a device for performing dilation of the larynx, trachea or bronchi.

BACKGROUND OF THE INVENTION

Management of stenosis of the trachea and bronchi, including laryngotracheal and subglottic stenosis, is one of the most challenging problems for the head and neck surgeon. Subglottic stenosis is a congenital or acquired narrowing of the subglottic airway. In the early twentieth century subglottic stenosis was rare, and most cases occurred in adults. In the 1960's the incidence of acquired subglottic stenosis began to dramatically increase in the neonatal population, most likely the result of increased survival of low-birth-weight infants and the increased use of intubation in this population. In addition, long term intubation has become an accepted alternative to tracheotomy, leading to more and more incidences of tracheal stenosis. Accordingly, the management of this condition has undergone a revolution, and reconstructive surgery efforts have been directed towards this population.

Most patients with stenosis of the airway are referred to and are treated at large academic centers by physicians specially trained in this area. There is a wide range of presentation of subglottic stenosis with similarities and differences in the pediatric age group compared to adults. If the stenosis is severe and congenital, the patient will show signs of airway distress at birth. More commonly, the pediatric patient with subglottic stenosis is a neonate in the intensive care unit who has failed extubation, usually multiple times. Occasionally patients will present in clinic with a tracheotomy and the report of some airway obstruction. Infants with mild subglottic stenosis may present with recurrent croup-like illnesses and poor feeding. Adults usually have a history of prior intubation with symptoms of progressive shortness of breath and noisy breathing.

Airway balloon dilation has been shown to be a safe and effective palliative procedure for treatment of mild congenital and acquired stenosis of the trachea and bronchi. Dilation of luminal human anatomy to treat stenoses can be dated back to the 16$^{th}$ Century with esophageal "bougie" dilation. Specific medical applications of luminal balloon dilation range from alimentary canal and airway dilation to dilation of the vasculature. Airway dilation dates back over 100 years ago with the invention and subsequent use of the first beveled rigid bronchoscopes for stricture management. The use of balloons to dilate airway strictures emerged in the mid-1980's with reports describing more specific utility of this procedure exclusively and in combination with other treatment modalities for airway stenosis. It was not until the early 1990's that the first balloon dilation involving flexible bronchoscopy was described.

Airway balloon dilation can be used to quickly re-establish tracheal or bronchial luminal patency to restore airflow in a way that doesn't cause excessive trauma to the patient. According to Poiseuille's Law, an increase in a tube's radius (such as the trachea or bronchus) can increase airflow by a power of 4 (airflow=radius of the tube$^4$). That is, very small increases in the luminal diameter of the airway can lead to large increases in airflow through the lungs. Literature has reported the use of balloon dilation for the treatment of benign strictures of the airway. Fibrotic strictures, such as those secondary to tuberculosis, long-term endotracheal or tracheostomy tube placement, berylliosis, Wegener's granulomatosis, or sarcoidosis have been shown to be treatable with airway balloon dilation therapy with general success. Additionally, balloon dilation has been useful in treating strictures secondary to major surgical interventions such as lung transplantation, sleeve resection, bronchial re-implantation, and lobectomy. For the purpose of treating strictures secondary to malignant obstruction, dilation therapy can be used alone or in combination with other techniques such as surgical resection, cryotherapy, laser therapy, and stent placement, depending on the desired outcome for the patient.

Treatment with airway dilation can involve the clinician inserting increasingly larger tubes into the airway (e.g. endotracheal tubes or cat-tail (bougie) dilators), which creates significant shear forces on the airway mucosa. Although safe when performed by a skilled clinician, such a procedure sometimes induces unwanted trauma to the airway in the form of deep lacerations and hemoptysis. Further, current dilation practices do not permit dilation of a tracheal stenosis that is distal to a narrowing of the proximal airway (i.e. a mild subglottic stenosis).

Current airway balloon dilation procedures are typically carried out using angioplasty balloons; however, several limitations to the use of angioplasty balloons become evident when used on the airway. For example, it may be difficult to adequately ventilate the patient during the dilation period, since the typical angioplasty balloon does not include a connection to an oxygen source. Further, the shape of the angioplasty balloon may predispose the balloon to slide out of place during dilation, or the balloon may be limited to the amount of pressure that can be applied before the balloon bursts. Also, the typical angioplasty balloon can usually stretch the airway lumen but not permanently dilate it. Other factors associated with failure of airway balloon dilation include previous attempts at endoscopic repair, circumferential scarring, and loss of cartilaginous support.

In light of the foregoing, it would be advantageous to provide a balloon dilator for the airway of a patient that is able to allow ventilation of the patient during balloon inflation. It would also be helpful to provide an airway balloon dilator that can provide increased inflation pressures during balloon dilation of the airway without balloon rupture. Further, it would be beneficial to provide a balloon that will not slip out of place in the patient's airway during balloon inflation. Finally, it is desirable to provide an airway balloon dilator that is capable of controlled cutting of scar tissue.

SUMMARY OF THE INVENTION

The present invention provides an airway balloon dilator for use to quickly re-establish laryngeal, tracheal or bronchial luminal patency to restore airflow in a way that avoids excessive trauma to the patient.

One aspect of the invention provides an apparatus for performing an airway balloon dilation procedure at the site of a stenosis in the airway of a patient, the apparatus comprising a central axis, a hollow core adapted to allow the patient to be ventilated therethrough, an inflatable outer balloon having an external surface, and at least one inflatable inner balloon, the apparatus being insertable into the airway of a patient for movement of the balloons therein between a deflated configuration and an inflated configuration, the at least one inner balloon configured to inflate inside the outer balloon yet separately from the outer balloon.

Another aspect of the invention provides a method for performing an airway balloon dilation procedure at the site of a stenosis in the airway of a patient, the method comprising: (1) inserting an apparatus into the airway, the apparatus including a central axis, a hollow core adapted to allow the patient to be ventilated therethrough, an inflatable outer balloon having an external surface, and at least one inflatable inner balloon, the apparatus being insertable into the airway of a patient for movement of the balloons therein between a deflated configuration and an inflated configuration, the at least one inner balloon configured to inflate inside the outer balloon yet separately from the outer balloon; (2) advancing the apparatus within the airway until the outer balloon is across the stenosis; and (3) inflating the balloon to cause and allow the external surface of the balloon to expand upon and dilate the stenosis.

Another aspect of the invention provides an apparatus for performing an airway balloon dilation procedure at the site of a stenosis in the airway of a patient, the apparatus comprising a central axis, a hollow core adapted to allow the patient to be ventilated therethrough, an inflatable, dumbbell-shaped outer balloon having an external surface, at least one inflatable inner balloon, a flexible support member mounted along the central axis of the apparatus and on the external surface of the outer balloon, the flexible support member being substantially compliant with the external surface of the outer balloon during movement therewith, and at least one microsurgical blade attached to the support member and adapted to form an effective cutting edge upon inflation of the outer balloon, the apparatus being insertable into the airway of a patient for movement of the balloons therein between a deflated configuration and an inflated configuration, the at least one inner balloon configured to inflate inside the outer balloon yet separately from the outer balloon, the dumbbell shape of the outer balloon adapted to hold the outer balloon in position over the stenosis, and the at least one blade adapted to form an effective cutting edge upon inflation of the outer balloon.

The nature and advantages of the present invention will be more fully appreciated from the following drawings, detailed description and claims.

BRIEF DESCRIPTION OF THE DRAWINGS

The accompanying drawings illustrate embodiments of the invention and, together with a general description of the invention given above, and the detailed description given below, serve to explain the principles of the invention.

DETAILED DESCRIPTION OF THE INVENTION

Figure 1:
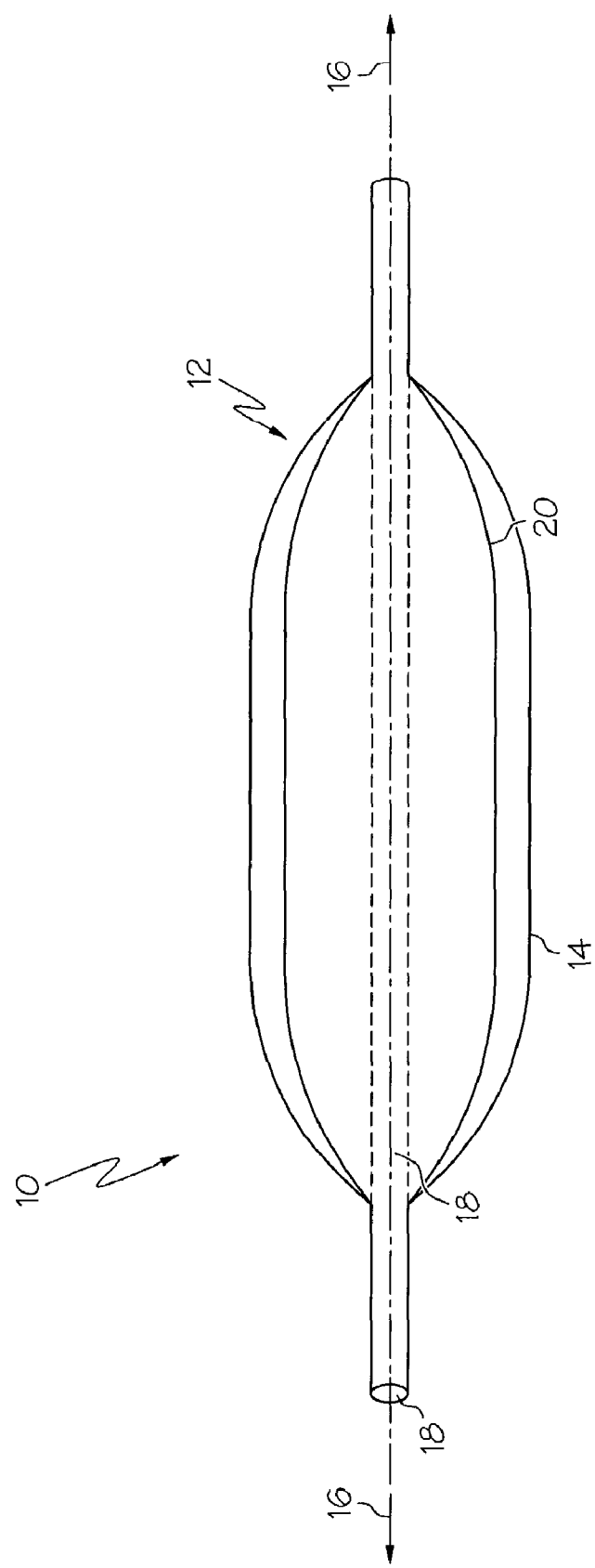
FIG. 1 is a perspective view of one embodiment of the balloon dilator of the present invention.

As illustrated in FIG. 1, one embodiment of the present invention is an apparatus 10 for performing an airway balloon dilation procedure at the site of a stenosis in the airway of a patient, the apparatus comprising an inflatable outer balloon 12 which has an external surface 14. The apparatus also comprises a central axis 16, a hollow core 18, and at least one inflatable inner balloon 20 adapted to inflate inside the outer balloon 12. The apparatus 10 is typically insertable into the airway of a patient for movement of the balloons 12, 20 between a deflated configuration and an inflated configuration. Further, the inner balloon 20 is designed to inflate inside the outer balloon 12 yet separately from the outer balloon, adding the ability of the apparatus to produce high dilation pressures without balloon rupture.

As shown in FIG. 1, the hollow core 18 traverses the entire apparatus 10. Typically the hollow core connects via a proximal ISO connector to an oxygen source such as an anesthesia circuit or the like, and is designed to allow the patient to be ventilated upon inflation of the balloons during the procedure, when the airway is otherwise occluded. The hollow core 18 is typically in the form of a central ventilating tube which is necessarily strong to prevent the pressure of the balloons from crushing the ventilating tube. The structure of the hollow core 18 is typically similar to a small endotracheal tube with a dilating cuff, and the tube may be reinforced, e.g. with wire, in the area of the cuff.

While standard balloon dilators typically have a very small central lumen to permit passage of a guidewire only, the balloon dilator of the present invention can have a fairly rigid (e.g. wire-reinforced) and relatively large central hollow core that can permit limited ventilation. For example, an 8.0 mm balloon dilator (i.e. having an outer diameter of 8.0 mm when inflated) can have a central ventilating lumen with a 2.0 mm inner diameter and a 3.0 mm outer diameter, while a 16 mm balloon dilator can have a central ventilating core with a 4.0 mm inner diameter and a 5.5 mm outer diameter.

Figure 2:
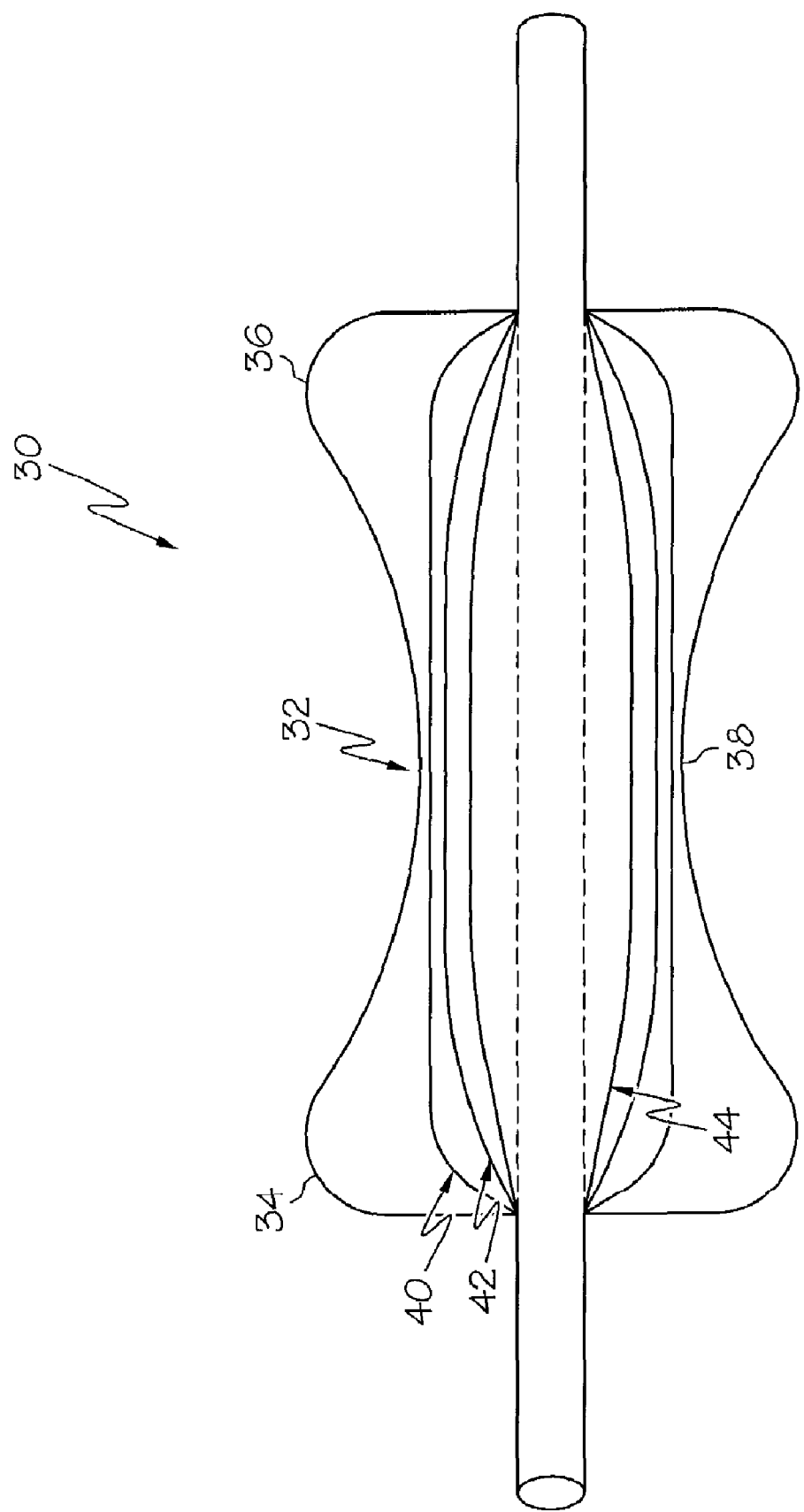
FIG. 2 is a perspective view of one embodiment of the balloon dilator in which the outer balloon has a dumbbell shape and multiple inner balloons.

As illustrated in FIG. 2, one embodiment of the invention is a balloon dilator apparatus 30 in which the inflatable outer balloon 32 is dumbbell-shaped. This dumbbell shape typically is created by making the proximal 34 and distal 36 ends of the balloon with a decreased balloon wall thickness as compared to the central section 38 of the balloon, which has a relatively increased balloon wall thickness. Alternatively, the central section 38 can have a flexible casing or layer of plastic or the like surrounding it (not shown), thereby preventing the central section 38 from dilating as quickly as the proximal and distal ends, 34, 36, yet still permitting complete inflation of the central section 38 at the higher inflation pressures.

The dumbbell shape prevents balloon slippage by inflating at either end (i.e. on either side of the stenosis) before the central section 38 inflates, and allows the central section 38 of the outer balloon 32 to stay in position over the stenosis during inflation. During inflation, the proximal 34 and distal 36 ends of the outer balloon 32 inflate first, forming the "dumbbell" shape, thereby trapping the stenotic airway segment at the central portion 38 of the balloon 32, so that the outer balloon 32 does not slip out of position. Then, as the pressure in the balloon is increased, the central portion 38 of the balloon fully inflates at the site of the stenosis.

The present invention can provide a balloon dilator with a rated burst pressure of up to 30 Atmospheres (atm). Generally, the larger the balloon diameter, the lower the burst pressure (e.g. for comparable Blue Max® angioplasty balloons, a 6.0 mm balloon has a rated burst pressure of 20 atm, while a 14.0 mm balloon has a rated burst pressure of 8 atm, and a 20.0 mm balloon has a rated burst pressure of 3.1 atm). To achieve this, the present invention provides an balloon which acts as an outer "sheath" that contains a series of inner balloons with smaller individual diameters that can tolerate a higher rated burst pressure than the outer balloon.

As shown in FIG. 2, the apparatus 30 can include a plurality of inner balloons 40, 42, 44. In the embodiment shown, inner balloon 44 is contained inside inner balloon 42, which is contained inside inner balloon 40. All of the inner balloons 40, 42, 44 are contained inside outer balloon 32, and are typically separately inflatable. Such an embodiment could be used with larger diameter outer balloons, e.g. between about 10 to about 20 mm. In this embodiment, the inner balloons 40, 42, 44 can be either dumbbell shaped or a "double cone" shape as seen with most angioplasty type balloons, and are inflated sequentially if higher pressures cannot be achieved by the outer balloon. Having a balloon dilator that incorporates multiple interconnected smaller balloons can achieve the desired pressure without risking balloon rupture during inflation. In another embodiment (not shown), the inner balloons 40, 42, 44 are all contained inside the outer balloon 32 but are not contained within one another. In this embodiment the inner balloons can be interconnected so that they all inflate simultaneously, like petals of a flower around the central core, within the outer balloon.

Figure 3:
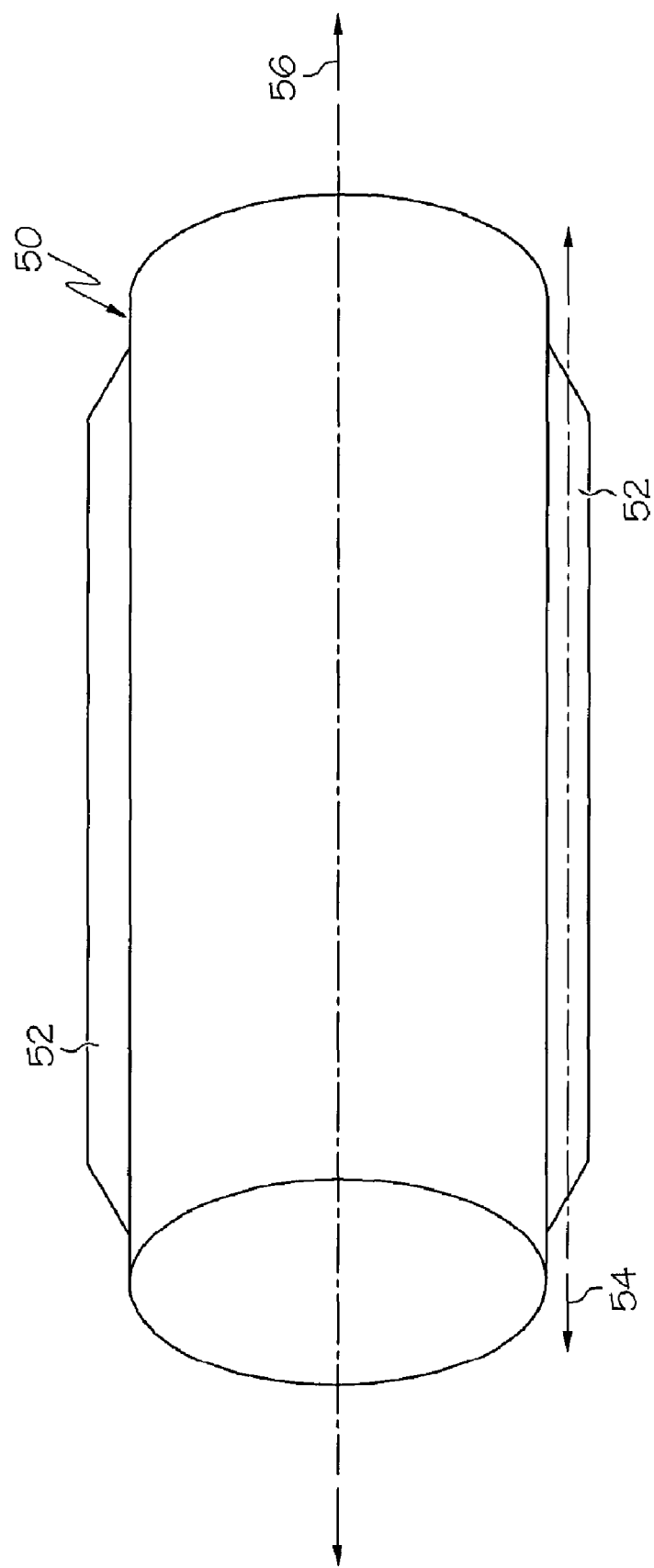
FIG. 3 is a perspective view of a flexible support member having microsurgical blades, the support member adapted to fit over the outer balloon according to one aspect of the invention.

As illustrated in FIG. 3, one embodiment of the invention can include a flexible support member 50 that can fit over the apparatus, specifically fitting over the outer balloon. The flexible support member 50 is typically made of a polyurethane material and includes a central axis 56 mounted along the central axis of the apparatus. The support member is adapted to fit over the external surface of the outer balloon, and is typically substantially compliant therewith during inflation and deflation. Support member 50 also includes at least one microsurgical blade, and in FIG. 3 two surgical blades 52 are attached. Blades 52 form an effective cutting edge upon inflation of the outer balloon. Blades 52 are typically made of stainless steel, and are elongated and permanently mounted on the flexible support member 50. In use, when the support member 50 is placed over the outer balloon, the blade axis 54 is parallel to the central axis 56 of the support member 50, which is substantially parallel to the central axis of the apparatus.

Having surgical blades 52 present on the apparatus during dilation typically permits controlled cutting or lysis of any scar tissue present in the patient's airway. The blades 52 should be clearly marked so that users can avoid inadvertently cutting themselves during placement of the support member 50 over the outer balloon. In one embodiment, the blades 52 lay flat on the surface of the support member prior to use and prior to inflation of the outer balloon 12, and then when the outer balloon reaches a certain pressure upon inflation the blades 52 will typically "stand up" or otherwise protrude or expose their cutting edge atop the flexible support member 50. Once fully deployed, the exposed edge of the blade 52 typically only protrudes between about 0.2 to about 0.4 mm, and the length of the blade is typically less than the length of the outer balloon 12. Typically there are a plurality of blades which are able to work together to embed into the stenosis or scar at a substantially uniform depth. For example, three blades could be permanently mounted on the flexible support member, each of the blades being separated from the other blades so that each blade is free to move from a relatively flat position to a cutting position on the flexible support member upon inflation of the outer balloon.

In practice, the airway balloon dilation procedure is typically performed at the site of a stenosis in the airway of a patient (i.e. the larynx, trachea or bronchi). Using the apparatus shown in FIG. 1, the surgeon or clinician first inserts the apparatus 10 into the airway, then advances the apparatus within the airway until the outer balloon 12 is across the stenosis. At this point, the surgeon or clinician inflates the outer balloon 12 to cause and allow the external surface 14 of the outer balloon 12 to expand upon and dilate the stenosis. To increase dilation pressures, the inner balloon 20 is then slowly inflated. Typically the inner balloon 20 is inflated after the inflation of the outer balloon 12. Under direct visualization, the balloons are typically inflated from between about 30 to about 120 seconds. The apparatus 10 can also be threaded over a guidewire (not shown) which fits through the hollow core 18 and is positioned across the stenosis. Repeat inflation-deflation cycles can be done if airway narrowing remains after the initial attempt.

During balloon dilation, the size of the balloon is first selected by the clinician, which depends upon the size of the stenosis in the patient's airway. The balloon size is typically between about 10 mm to about 40 mm in length. The outer balloon is positioned over the stenosis and then each balloon is individually dilated to the desired pressure with a balloon pump, typically to between about 8 to about 20 atmospheres. After these pressures are maintained for a predetermined period of time, typically between about 60 to about 180 seconds, the balloons are deflated and the clinician determines if repeat inflation is necessary. Repeat inflation can be safely performed if there is no obvious trauma to the airway.

While the balloon dilator of the present invention typically allows ventilation while inflated, the balloon dilator can also be manufactured without an inner hollow core for ventilation, but simply with a small lumen large enough to pass a guidewire. The advantage of such an embodiment is that the un-inflated balloon without a hollow core for ventilation is typically much "skinnier" and can pass through a very small hole (lumen) in the trachea or airway easier than a balloon dilator with a hollow core adapted to allow the patient to be ventilated therethrough.

While the present invention has been illustrated by the description of embodiments and examples thereof, it is not intended to restrict or in any way limit the scope of the appended claims to such detail. Additional advantages and modifications will be readily apparent to those skilled in the art. Accordingly, departures may be made from such details without departing from the scope or spirit of the invention.

What is claimed is:

1. An apparatus for performing an airway balloon dilation procedure at the site of a stenosis in the airway of a patient, the apparatus comprising:
   a central axis;
   a hollow core adapted to allow the patient to be ventilated therethrough;
   an inflatable outer balloon having an external surface; and
   at least one inflatable inner balloon,
   the apparatus being insertable into the airway of a patient for movement of the balloons therein between a deflated configuration and an inflated configuration, the at least one inner balloon configured to inflate inside the outer balloon yet separately from the outer balloon, wherein during inflation the balloon pressures are between about 3 atmospheres and about 30 atmospheres.

2. The apparatus according to claim 1, wherein the inflatable outer balloon is dumbbell-shaped to hold the outer balloon in position over the stenosis, the hollow core is only large enough to allow passage of a guidewire therethrough, and the hollow core does not allow the patient to be ventilated therethrough.

3. The apparatus according to claim 1, comprising a plurality of inner balloons.

4. The apparatus according to claim 3, wherein there are three inner balloons including a first inner balloon contained inside a second inner balloon, the second inner balloon being contained inside a third inner balloon, all inner balloons being contained inside the outer balloon and being separately inflatable.

5. The apparatus according to claim 3, including a plurality of inflatable inner balloons, wherein all inner balloons are contained inside the outer balloon and are simultaneously inflatable within the outer balloon.

6. The apparatus according to claim 1, further comprising a flexible support member mounted along the central axis of the apparatus and on the external surface of the outer balloon, the flexible support member being substantially compliant with the external surface of the outer balloon during movement therewith, and at least one microsurgical blade attached to the support member and adapted to form an effective cutting edge upon inflation of the outer balloon.

7. The apparatus according to claim 6, wherein the apparatus comprises a plurality of blades adapted to embed into the stenosis at a substantially uniform depth.

8. The apparatus according to claim 6, wherein the support member is made of a polyurethane material and the at least one blade is made of stainless steel.

9. The apparatus according to claim 6, wherein the hollow core is only large enough to allow passage of a guidewire therethrough.

10. The apparatus according to claim 6, wherein the at least one blade includes a blade axis, the at least one blade being elongated and mounted on the support member with the blade axis substantially parallel to the central axis of the apparatus.

11. A method for performing an airway balloon dilation procedure at the site of a stenosis in the airway of a patient, the method comprising the steps of:
  (1) inserting an apparatus into the airway, the apparatus including a central axis, a hollow core adapted to allow the patient to be ventilated therethrough, an inflatable outer balloon having an external surface, and at least one inflatable inner balloon, wherein the inner diameter of the hollow core is from about 2.0 mm to about 3.0 mm, the apparatus being insertable into the airway of a patient for movement of the balloons therein between a deflated configuration and an inflated configuration, the at least one inner balloon configured to inflate inside the outer balloon yet separately from the outer balloon;
  (2) advancing the apparatus within the airway until the outer balloon is positioned within the area of the stenosis; and
  (3) inflating the balloons to cause and allow the external surface of the balloon to expand upon and dilate the stenosis, wherein during inflation the balloon pressures are between about 3 atmospheres and about 30 atmospheres.

12. The method according to claim 11, wherein the apparatus further comprises a flexible support member mounted along the central axis of the apparatus and on the external surface of the outer balloon, the flexible support member being substantially compliant with the external surface of the outer balloon during movement therewith, and at least one microsurgical blade attached to the support member and adapted to form an effective cutting edge upon inflation of the outer balloon, wherein the inflating step allows the at least one blade to form an effective cutting edge upon inflation of the outer balloon.

13. The method according to claim 12, wherein the flexible support member comprises a plurality of blades adapted to embed into the stenosis at a substantially uniform depth.

14. The method according to claim 11, wherein the advancing step comprises the steps of:
  (i) inserting a guidewire into the airway of the patient; and
  (ii) tracking the guidewire with the apparatus to position the outer balloon across the stenosis.

15. The method according to claim 11, further comprising the steps of:
  (4) deflating the balloons after a predetermined amount of time;
  (5) repeating steps (1) through (4) if airway narrowing remains after the initial attempt to dilate the stenosis fails; and
  (6) removing the apparatus from the patient.

16. An apparatus for performing an airway balloon dilation procedure at the site of a stenosis in the airway of a patient, the apparatus comprising:
  a central axis;
  a hollow core adapted to allow the patient to be ventilated therethrough, wherein the inner diameter of the hollow core is from about 2.0 mm to about 3.0 mm;
  an inflatable, dumbbell-shaped outer balloon having an external surface;
  at least one inflatable inner balloon, wherein during inflation the balloon pressures are between about 3 atmospheres and about 30 atmospheres;
  a flexible support member mounted along the central axis of the apparatus and on the external surface of the outer balloon, the flexible support member being substantially compliant with the external surface of the outer balloon during movement therewith; and
  at least one microsurgical blade attached to the support member and adapted to form an effective cutting edge upon inflation of the outer balloon,
the apparatus being insertable into the airway of a patient for movement of the balloons therein between a deflated configuration and an inflated configuration, the at least one inner balloon configured to inflate inside the outer balloon yet separately from the outer balloon, the dumbbell shape of the outer balloon adapted to hold the outer balloon in position over the stenosis, and the at least one blade adapted to form an effective cutting edge upon inflation of the outer balloon.

17. The apparatus according to claim 16, wherein the apparatus comprises a plurality of blades adapted to embed into the stenosis at a substantially uniform depth.

18. The apparatus according to claim 16, wherein the support member is made of a polyurethane material, the at least one blade is made of stainless steel, the hollow core is only large enough to allow passage of a guidewire therethrough, and the hollow core does not allow the patient to be ventilated therethrough.

19. The apparatus according to claim 16 wherein the at least one blade includes a blade axis, the at least one blade being elongated and mounted on the support member with the blade axis substantially parallel to the central axis of the apparatus.

20. The apparatus according to claim 16, including a plurality of inflatable inner balloons, wherein all inner balloons are contained inside the outer balloon and are simultaneously inflatable within the outer balloon.

* * * * *